(12) United States Patent
Williams (10) Patent No.: US 11,147,560 B2
(45) Date of Patent: Oct. 19, 2021

(54) BUTTRESS FOR CIRCULAR EEA STAPLERS

(71) Applicant: Covidien LP, Mansfield, MA (US)

(72) Inventor: Justin Williams, Southbury, CT (US)

(73) Assignee: Covidien LP, Mansfield, MA (US)

( * ) Notice: Subject to any disclaimer, the term of this patent is extended or adjusted under 35 U.S.C. 154(b) by 190 days.

(21) Appl. No.: 16/598,017

(22) Filed: Oct. 10, 2019

(65) Prior Publication Data

US 2020/0138440 A1    May 7, 2020

Related U.S. Application Data

(60) Provisional application No. 62/756,710, filed on Nov. 7, 2018.

(51) Int. Cl.
| | |
|---|---|
| *A61B 17/3209* | (2006.01) |
| *A61B 17/115* | (2006.01) |
| *A61B 17/00* | (2006.01) |
| *A61B 17/11* | (2006.01) |

(52) U.S. Cl.
CPC ...... *A61B 17/1155* (2013.01); *A61B 17/3209* (2013.01); *A61B 2017/00004* (2013.01); *A61B 2017/1132* (2013.01)

(58) Field of Classification Search
CPC ................ A61B 17/1155; A61B 17/3209
USPC ...................................................... 227/180.1
See application file for complete search history.

(56) References Cited

U.S. PATENT DOCUMENTS

| | | |
|---|---|---|
| 4,473,077 A | 9/1984 | Noiles et al. |
| 4,576,167 A | 3/1986 | Noiles |
| 4,646,745 A | 3/1987 | Noiles |
| 5,005,749 A | 4/1991 | Aranyi |
| 5,053,390 A | 10/1991 | Benoit et al. |
| 5,119,983 A | 6/1992 | Green et al. |
| 5,588,579 A | 12/1996 | Schnut et al. |
| 2009/0001122 A1 | 1/2009 | Prommersberger et al. |

(Continued)

FOREIGN PATENT DOCUMENTS

| | | |
|---|---|---|
| EP | 2604195 A1 | 6/2013 |
| EP | 2604197 A2 | 6/2013 |

(Continued)

OTHER PUBLICATIONS

Extended European Search Report issued in EP Application No. 19207351.8, dated Feb. 19, 2020.

*Primary Examiner* — Nathaniel C Chukwurah
(74) *Attorney, Agent, or Firm* — Carter DeLuca & Farrell LLP (57) ABSTRACT

A stapling apparatus includes a cartridge assembly, an anvil assembly, and a buttress material. The cartridge assembly includes pushers configured to eject the respective surgical staples from the cartridge assembly, and an outer wall defining a cavity and having a finger deflectably extending over the cavity. The buttress material includes an annular body and a tab extending proximally from the annular body such that at least a portion of the tab is wrapped around the finger of the outer wall of the staple cartridge assembly. The pushers are movable between a first position in which one of the pushers engages the finger such that the tab is secured against the one of the pushers, and a second position in which the one of the pushers is disengaged from the finger such that a portion of the tab is released from the one of the pushers.

15 Claims, 4 Drawing Sheets

(56) References Cited

U.S. PATENT DOCUMENTS

| | | | |
|---|---|---|---|
| 2013/0153634 A1* | 6/2013 | Carter | A61B 17/1155 227/176.1 |
| 2013/0153639 A1* | 6/2013 | Hodgkinson | A61B 17/1155 227/180.1 |
| 2018/0360460 A1 | 12/2018 | Mozdzierz et al. | |

FOREIGN PATENT DOCUMENTS

| | | |
|---|---|---|
| EP | 2620107 A1 | 7/2013 |
| EP | 3563777 A2 | 11/2019 |

* cited by examiner

BUTTRESS FOR CIRCULAR EEA STAPLERS

CROSS-REFERENCE TO RELATED APPLICATIONS

This application claims the benefit of and priority to U.S. Provisional Patent Application Ser. No. 62/756,710 filed Nov. 7, 2018, the entire disclosure of which is incorporated by reference herein.

BACKGROUND

Technical Field

The present disclosure relates to a surgical apparatus for applying surgical fasteners or staples to body tissue, and more particularly, to a surgical buttress for use with an end-to-end anastomosis stapling apparatus.

Background of Related Art

Anastomosis is a surgical joining of separate hollow organ sections. Typically, an anastomosis procedure follows surgery in which a diseased or defective section of hollow tissue is removed and the remaining end sections are joined. Depending on the desired anastomosis procedure, the end sections may be joined by either circular, end-to-end or side-to-side organ reconstruction methods.

In a circular anastomosis procedure, the two ends of the organ sections are joined by means of a stapling apparatus, which drives a circular array of staples through the end section of each organ section and simultaneously cores any tissue interior of the driven circular array of staples to free the tubular passage. Typically, these apparatuses include an elongated shaft having a handle portion at a proximal end to actuate the apparatus and a staple holding component disposed at a distal end. An anvil assembly including an anvil shaft with attached anvil head is mounted to the distal end adjacent the staple holding component. Opposed end sections of the organ to be stapled are clamped between the anvil head and the staple holding component. The clamped tissue is stapled by driving a plurality of staples from the staple holding component so that the ends of the staples pass through the tissue and are deformed by the anvil head.

In use, one end section of the organ is secured about the anvil assembly and the other end section of the organ is held in place adjacent the staple holding component. The shaft of the anvil assembly is removably connected to the apparatus. Once the anvil shaft is secured to the apparatus, the anvil is drawn into close approximation to the staple holding component. The apparatus is then fired to cause the staples to pass through tissue of both sections of the organ and deform against the anvil. During the firing step, a circular knife is advanced to cut tissue inside the staple line, thereby establishing a passage between the two sections of the organ. After firing, the apparatus is typically removed by withdrawing the anvil through the staple line, after which the surgeon will carefully inspect the surgical site to ensure a proper anastomosis has been achieved.

In certain surgical procedures, buttress or reinforcing materials have been utilized in connection with circular stapling apparatuses. However, due to the inherent difficulty in positioning and securing such materials with the apparatus, a need exists for the buttress material that can be safely and effectively positioned within a staple cartridge assembly.

SUMMARY

In accordance with an embodiment of the present disclosure, an apparatus for joining two hollow organ sections with an annular array of surgical staples includes a staple cartridge assembly, an anvil assembly, and a buttress material. The staple cartridge assembly is configured to support the annular array of surgical staples therein. The staple cartridge assembly includes pushers configured to eject the respective surgical staples from the staple cartridge assembly, and an outer wall defining a cavity and having a finger deflectably extending over the cavity. The anvil assembly is movable relative to the staple cartridge assembly between spaced apart and approximated positions to adjustably clamp the two hollow organ sections between the staple cartridge and anvil assemblies. The buttress material includes an annular body dimensioned to be mounted on a distal surface of the staple cartridge assembly, and a tab extending proximally from the annular body such that at least a portion of the tab is wrapped around the finger of the outer wall of the staple cartridge assembly. The pushers are movable between a first position in which one of the pushers engages the finger such that the tab of the buttress material wrapped around the finger is secured against the pusher, and a second position in which the one of the pushers is disengaged from the finger such that the at least a portion of the tab of the buttress material wrapped around the finger is released from the one of the pushers.

In an embodiment, the finger may be radially deflectable.

In another embodiment, the finger may be biased radially inward.

In yet another embodiment, the annular body of the buttress material may include a planar surface configured to be in planar contact with the distal surface of the staple cartridge assembly.

In still yet another embodiment, the buttress material may include first and second tabs diametrically opposing each other.

In an embodiment, the finger of the outer wall of the staple cartridge assembly may include a tooth configured to support the at least a portion of the tab against the one of the pushers.

In another embodiment, one of the pushers may include an engaging portion configured to engage the finger of the outer wall of the staple cartridge assembly. The engaging portion may be axially tapered.

In yet another embodiment, the annular array of surgical staples may be ejected from the staple cartridge assembly when the one of the pushers is in the second position.

In still yet another embodiment, the annular body of the buttress material may be concentrically disposed in a juxtaposed relation with the annular array of surgical staples.

In still yet another embodiment, the staple cartridge assembly may further include a cylindrical knife disposed radially inward of the buttress material.

In accordance with another embodiment of the present disclosure, an apparatus for joining two hollow organ sections with an annular array of surgical staples includes a staple cartridge assembly, an anvil assembly, and a buttress material. The staple cartridge assembly includes the annular array of surgical staples and pushers configured to eject the annular array of surgical staples from the staple cartridge assembly. The anvil assembly is movable relative to the staple cartridge assembly between spaced apart and approximated positions to adjustably clamp the two hollow organ sections between the staple cartridge and anvil assemblies. The buttress material includes a body and a tab extending from the body. The body is disposed on the staple cartridge assembly such that the body and the annular array of surgical staples are in superposed relation. At least one pusher is transitionable between a first position in which the at least one pusher engages the tab to secure the buttress material to the staple cartridge assembly and a second position in which the at least one pusher is disengaged from the tab to release the buttress material from the staple cartridge assembly.

BRIEF DESCRIPTION OF THE DRAWINGS

Various embodiments of the present disclosure are described hereinbelow with reference to the drawings, wherein.

DETAILED DESCRIPTION OF EMBODIMENTS

Embodiments of the present disclosure will now be described in detail with reference to the drawings, in which like reference numerals designate identical or corresponding elements in each of the several views. As used herein, the term "distal," as is conventional, will refer to that portion of the apparatus, apparatus, device or component thereof which is farther from the user while, the term "proximal," will refer to that portion of the apparatus, apparatus, device or component thereof which is closer to the user. In the following description, well-known functions or constructions are not described in detail to avoid obscuring the present disclosure in unnecessary detail.

Figure 1:
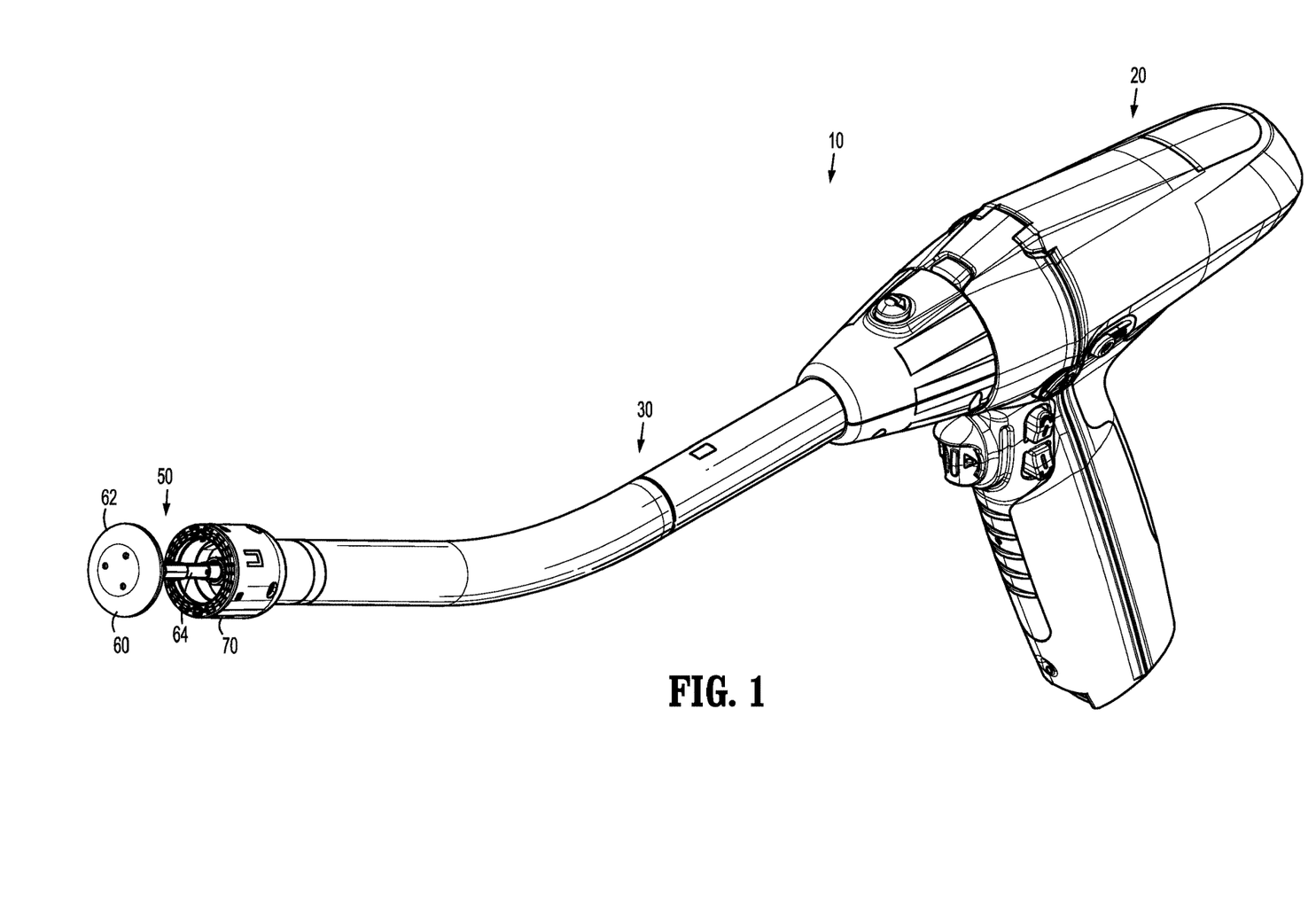
FIG. 1 is a perspective view of a surgical stapling apparatus configured for use with a surgical buttress material in accordance with an embodiment of the present disclosure.

With reference to FIG. 1, a surgical stapling apparatus 10 for performing circular anastomosis of hollow organs is shown. The surgical stapling apparatus 10 drives a circular array of staples 11 (FIG. 5) through the end sections of each organ and simultaneously fires a cylindrical knife 76 (FIG. 2) to core any tissue radially inward of the driven circular array of staples 11 to free the tubular passage, and thereby joining two ends of the organ. The staples 11 are of a conventional type and include a backspan having a pair of legs extending from the backspan. The legs terminate in tissue penetrating tips. The surgical stapling apparatus 10 includes a powered electromechanical handle assembly 20, an adapter assembly 30 extending distally from the powered electromechanical handle assembly 20, and a reload 50 selectively coupled with the adapter assembly 30. In particular, the reload 50 includes an anvil assembly 60, a staple cartridge assembly 70, and a surgical buttress material 100 (FIG. 2) releasably attachable to the staple cartridge assembly 70 in accordance with an embodiment of the present disclosure. The components of the surgical stapling apparatus 10 are generally formed from thermoplastics including polycarbonates, and metals including stainless steel and aluminum. The particular material selected to form a particular component may depend upon the strength requirements of the particular component.

With continued reference to FIG. 1, the powered electromechanical handle assembly 20 can be actuated to approximate the anvil assembly 60 relative to the staple cartridge assembly 70 and to apply a plurality of annular arrays of staples 11 (FIG. 5) through tissue. The anvil assembly 60 is axially movable relative to the staple cartridge assembly 70 between a spaced apart position and an approximated position, in which, the anvil assembly 60 is positioned adjacent the staple cartridge assembly 70 to clamp tissue therebetween. The powered electromechanical handle assembly 20 may be actuated to fire the staples 11 through tissue to join two segments of tubular tissues together.

With continued reference to FIG. 1, the adapter assembly 30 is constructed to have a slightly curved/bent shape along its length. However, the adapter assembly 30 may also be straight, as well as flexible to bend to any configuration. The length, shape and/or the diameter of the adapter assembly 30 may be tailored to suit a particular surgical procedure.

Examples of apparatuses for performing circular anastomosis of hollow organs are described in U.S. Pat. Nos. 6,053,390, 5,588,579, 5,119,983, 5,005,749, 4,646,745, 4,576,167, and 4,473,077 and U.S. patent application Ser. No. 15/972,606, filed May 7, 2018, each of which is incorporated herein in its entirety by reference. While a powered stapling apparatus is shown and described herein, it is contemplated and within the scope of the present disclosure that the stapling apparatus may be a manually actuated apparatus capable of performing circular anastomosis.

Figure 2:
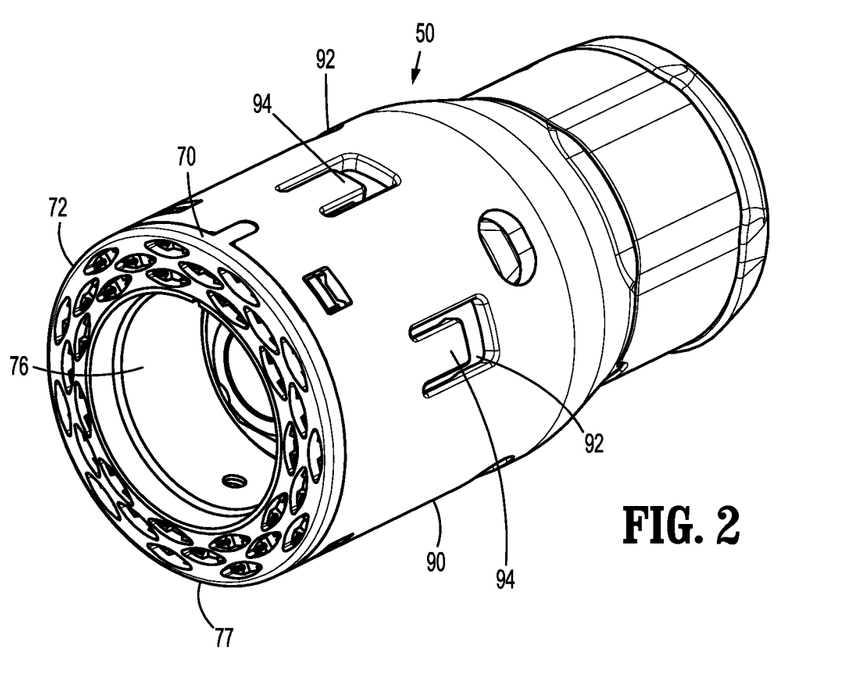
FIG. 2 is a perspective view of a staple cartridge assembly of the surgical stapling apparatus of FIG. 1.
Figure 3:
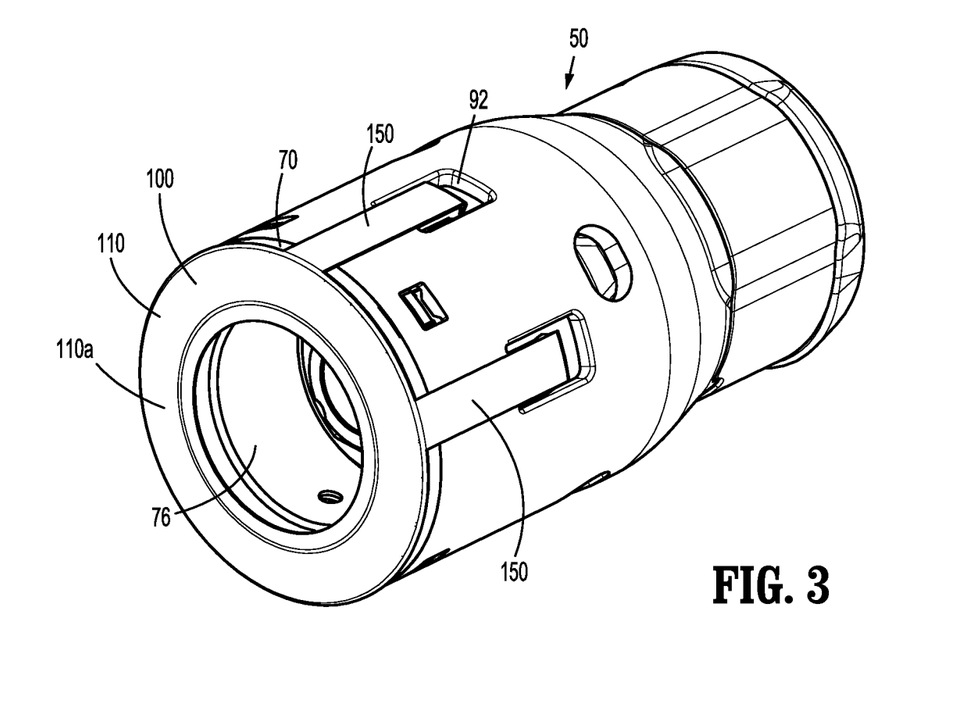
FIG. 3 is a perspective view of the staple cartridge assembly and a buttress material mounted on the staple cartridge assembly in accordance with an embodiment of the present disclosure.

With reference to FIG. 1-3, the reload 50 includes the anvil assembly 60, the staple cartridge assembly 70, and the surgical buttress material 100 detachably secured with the staple cartridge assembly 70. The staple cartridge assembly 70 may be fixedly connected to a distal end portion of the reload 50 or may be configured to concentrically fit within the distal end portion of the reload 50. In particular, the staple cartridge assembly 70 defines a plurality of annular arrays of staple receiving slots 72 having a staple 11 (FIG. 5) disposed in each one of the staple receiving slots 72.

In addition, the staple cartridge assembly 70 includes the cylindrical knife 76 concentrically arranged with the annular arrays of staples 11 (FIG. 5) and a plurality of staple pushers 33 (FIG. 5) each disposed in the corresponding staple receiving slot 72 to eject the corresponding staple 11 through the staple receiving slot 72. The cylindrical knife 76 (FIG. 5) includes a distal rim 79 defining a knife blade adapted to cut tissue. In use, the staples 11 travel through the staple receiving slots 72 and tissue towards the anvil assembly 60 for formation thereof. Upon actuation of the powered electromechanical handle assembly 20, the cylindrical knife 76 is moved distally to cut tissue, and the plurality of pushers 33 (FIG. 5) are moved distally to eject the staples 11 from the staple receiving slots 72, towards the anvil assembly 60.

Positioned distally of the staple cartridge assembly 70 (FIG. 1) is the anvil assembly 60 including an anvil member 62 and a shaft 64 extending proximally from the anvil member 62. The anvil member 62 further defines a plurality of pockets (not shown) for receiving and forming the staples 11. The shaft 64 is configured to be detachably received in an approximation shaft 75 (FIG. 5) of the staple cartridge assembly 70. The approximation shaft 75 is operatively coupled with the powered electromechanical handle assembly 20 for axial displacement thereof. Such axial movement of the approximation shaft 75 is imparted to the anvil assembly 60 detachably coupled with the approximation shaft 75. In this manner, the anvil assembly 60 is movable axially relative to the staple cartridge assembly 70 between the spaced apart position and the approximated position, in which, the anvil assembly 60 is positioned adjacent the staple cartridge assembly 70 to adjustably clamp tissue between the anvil assembly 60 and the staple cartridge assembly 70.

With reference now to FIGS. 2 and 3, the staple cartridge assembly 70 includes an outer wall 90 defining circumferentially arranged cavities 92. The outer wall 90 includes fingers 94 extending over the respective cavities 92. Each finger 94 is radially deflectable to selectively secure a portion of the surgical buttress material 100, as will be described hereinbelow. In particular, each finger 94 may be biased radially inward in order to secure the portion of the surgical buttress material 100 to the staple cartridge assembly 70. In addition, each finger 94 may include a tooth 95 (FIG. 6) extending radially inward such that the tooth 95 engages and urges a portion of the surgical buttress material 100 radially inward in order secure the surgical buttress material 100 against the pusher 33.

Figure 4:
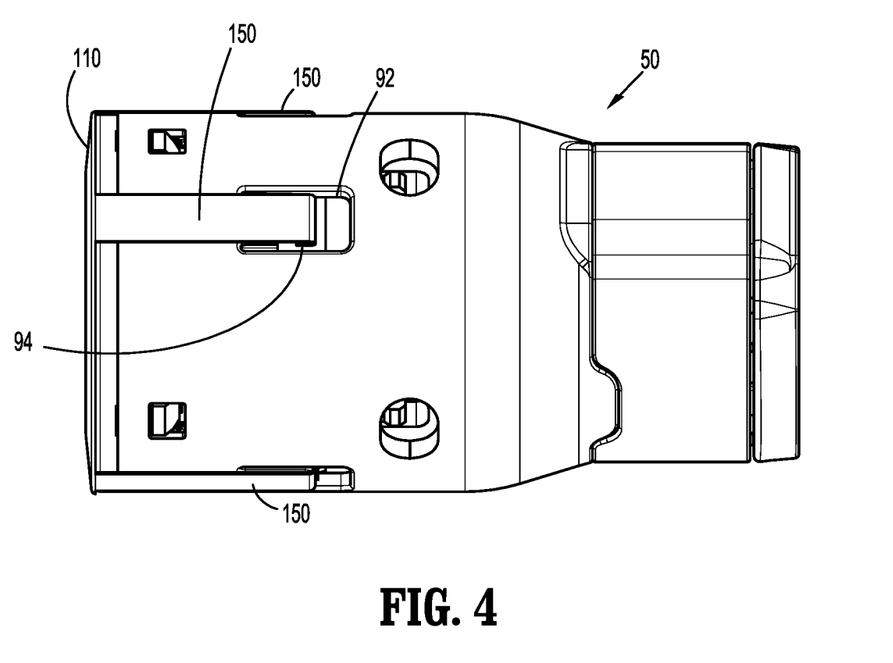
FIG. 4 is a side view of the staple cartridge assembly and the buttress material of FIG. 3.

With reference now to FIGS. 2-4, the surgical buttress material 100 includes an annular body 110 and circumferentially arranged tabs 150. For example, the surgical buttress material 100 may include at least two tabs 150 diametrically opposing each other. The annular body 110 is provided to reinforce and seal staple lines applied to tissue by the surgical stapling apparatus 10. The annular body 110 may be concentrically aligned with the staple cartridge assembly 70. In addition, the annular body 110 is dimensioned to be flush with an outer peripheral edge of the staple cartridge assembly 70 when mounted on the staple cartridge assembly 70. The annular body 110 defines a planar surface 110a configured to be in registration with a distal surface 77 of the staple cartridge assembly 70. Under such a configuration, the annular body 110 is in registration with the plurality of annular arrays of the staple receiving slots 72. In this manner, when the staples 11 are ejected through the plurality of annular arrays of the staple receiving slots 72, the legs of each staple 11 penetrate through the annular body 110 and the backspan of staple 11 is secured or abuts against a proximal surface of the annular body 110. The surgical buttress member 100 is positioned radially outward of the cylindrical knife 76. As such, severing of the surgical buttress material 100 by the cylindrical knife 76 is eliminated.

The circumferentially arranged tabs 150 extend axially along the outer wall 90 of the staple cartridge assembly 70. Each tab 150 includes a free end portion 150a (FIG. 7) dimensioned to be wrapped around a corresponding finger 94 of the outer wall 90.

The annular body 110 and the circumferentially arranged tabs 150 of the surgical buttress material 100 may be monolithically formed as a single construct. The surgical buttress material 100 may be fabricated from a biocompatible material which is bio-absorbable or non-absorbable, as well as natural or synthetic materials. It should be understood that any combination of natural, synthetic, bio-absorbable, and non-bioabsorbable materials may be used to form the surgical buttress material 100. In addition, the surgical buttress material 100 may be porous, non-porous, or combinations thereof. It is also envisioned that the surgical buttress material 100 described herein may contain a plurality of layers in which any combination of non-porous and porous layers may be configured. For example, the surgical buttress material 100 may be formed to include multiple non-porous layers and porous layers that are stacked in an alternating manner. In another example, the surgical buttress material 100 may be formed in a "sandwich-like" manner wherein the outer layers of surgical buttress material 100 may include porous layers and the inner layers are non-porous layers. Examples of multi-layered buttress members are disclosed in U.S. Patent Application Publication No. 2009/0001122, filed on Jun. 27, 2007, entitled "Buttress and Surgical Stapling Apparatus," the entire disclosure of which is incorporated by reference therein.

In particular, the use of non-porous layers in the surgical buttress material 100 may enhance the ability of the surgical buttress material 100 to resist tears and perforations during the manufacturing, shipping, handling, and stapling processes. In addition, the use of a non-porous layer in the surgical buttress may also retard or inhibit tissue ingrowth from surrounding tissues, and thereby acting as an adhesion barrier and inhibiting the formation of unwanted scar tissue.

In addition, at least one bioactive agent may be combined with the surgical buttress material 100. The agent may be disposed on a surface of the surgical buttress and/or impregnated therein. In these embodiments, the surgical buttress material 100 may also serve as a vehicle for delivery of the bioactive agent. The term "bioactive agent," as used herein, is used in its broadest sense and includes any substance or mixture of substances that have clinical use.

Figure 5:
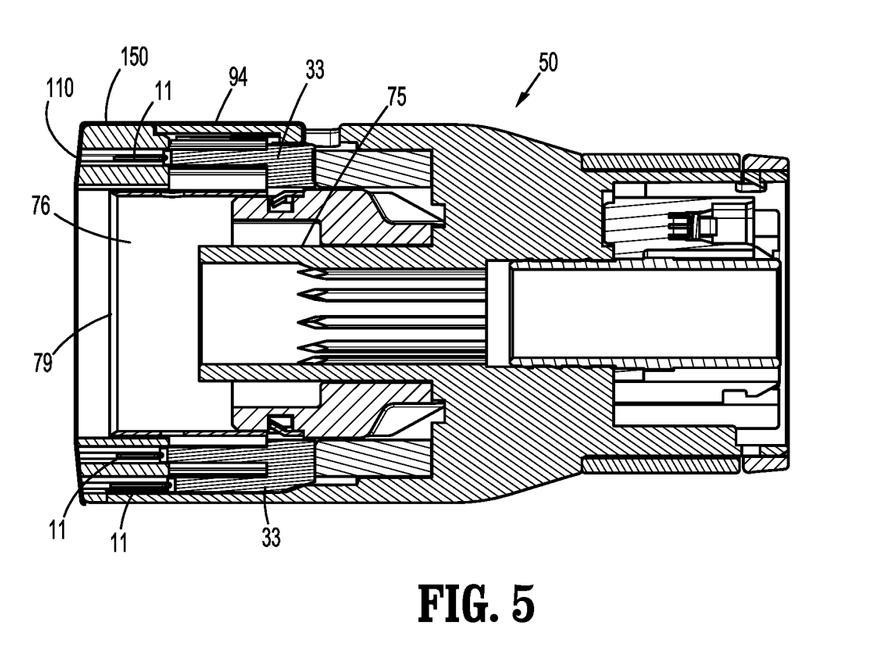
FIG. 5 is a side cross-sectional view of the staple cartridge and the buttress material of FIG. 4.
Figure 6:
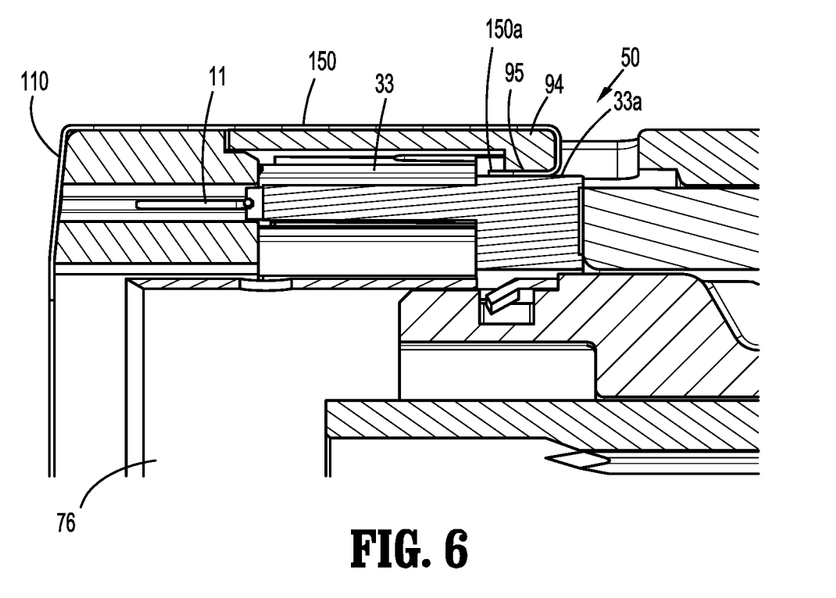
FIG. 6 is a partial side cross-sectional view of the staple cartridge and the buttress material of FIG. 5, illustrating a pusher securing the buttress material thereto.
Figure 7:
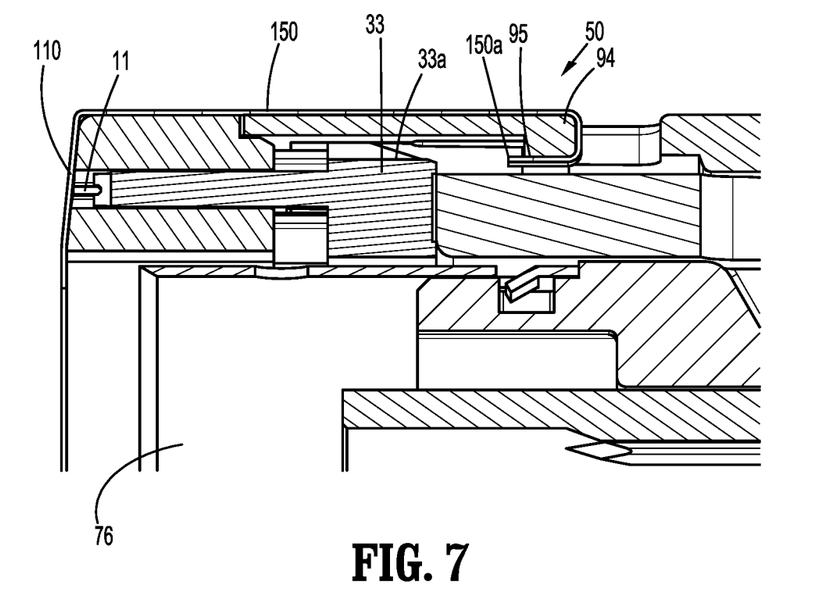
FIG. 7 is a partial side cross-sectional view of the staple cartridge and the buttress material of FIG. 6, illustrating the pusher disengaged from the buttress material.

With reference now to FIGS. 5-7, the surgical buttress material 100 is selectively detachable from the staple cartridge assembly 70 due to the flexible nature of the finger 94, as discussed hereinabove. In particular, prior to axial advancement of the pushers 33, i.e., prior to firing of the staples 11, the pushers 33 are in a proximal position (FIG. 6). Each pusher 33 includes an engaging portion 33a. At this time, the engaging portion 33a engages the tooth 95 of the finger 94 of the outer wall 90. Under such a configuration, the free end portion 150a of the tab 150 wrapped around the finger 94 is interposed between the finger 94 and the engaging portion 33a of the pusher 33. In this manner, the tabs 150 of the surgical buttress material 100 are secured with the staple cartridge assembly 70 such that the annular body 110 is firmly attached to the distal surface 77 of the staple cartridge assembly 70.

With particular reference now to FIG. 7, when the pusher 33 is advanced in a distal direction such that the staples 11 are ejected from the staple receiving slots 72 (FIG. 2), the engaging portion 33a of the pusher 33 disengages from the free end portion 150a of the tab 150 and the finger 94 of the outer wall 90. At this time, the surgical buttress material 100 now stapled to tissue is released from the staple cartridge assembly 70. In order to facilitate engagement and disengagement of the engaging portion 33a of the pusher 33 and the finger 94 of the outer wall 90, the engaging portion 33a may be axially tapered. It is further contemplated that the tooth 95 may also be tapered to further facilitate engagement and disengagement of the engaging portion 33a and the finger 94.

In use, the annular body 110 of the surgical buttress material 100 is mounted on the distal surface 77 of the staple cartridge assembly 70 such that the annular body 110 is superposed with the annular arrays of the staple receiving slots 72. In this manner, when the staples 11 are ejected through the annular arrays of the staple receiving slots 72, the legs of each staple 11 penetrate through the annular body 110 of the surgical buttress material 100 and the backspan of staple 11 is secured or abuts against a proximal surface of the annular body 110. Thereafter, the free end portions 150a of the tabs 150 are wrapped around the respective fingers 94 of the outer wall 90 of the staple cartridge assembly 70 such that the surgical buttress material 100 is firmly attached to the staple cartridge assembly 70.

The surgical stapling apparatus 10 is used in an anastomosis procedure to effect joining of, for example, two opposing intestinal sections. The anastomosis procedure is typically performed using minimally invasive surgical techniques including laparoscopic means and instrumentation. Initially, a diseased intestinal section is removed. Thereafter, the anvil assembly 60 is inserted to the operative site either through a surgical incision or transanally and is positioned within a first intestinal section. The adapter assembly 20 of the surgical stapling apparatus 10, having the staple cartridge assembly 70 attached thereto, is inserted transanally into a second intestinal section. The first and second intestinal sections are then temporarily secured about their respective components (e.g., shaft 64 of anvil assembly 60 and the staple cartridge assembly 70) by conventional means such as a purse string suture (not shown).

Thereafter, the clinician maneuvers the anvil assembly 60 until the proximal end of the shaft 64 is inserted into and attached/connected to the distal end of the approximation shaft 75 of the staple cartridge assembly 70. The shaft 64 engages the approximation shaft 75 to be operable as a unitary construct. The anvil assembly 60 and the staple cartridge assembly 70 are then approximated to approximate the first and second intestinal sections. At this time, the surgical buttress material 100 is firmly attached to the staple cartridge assembly 70. The surgical stapling apparatus 10 is then fired causing the plurality of staple pushers 33 disposed in respective staple receiving slot 72 to eject the staples 11 through the respective slots 72. The staples 11 travel through the first and second intestinal sections as well as the annular body 110 of the surgical buttress material 100, towards the anvil assembly 60, thereby effecting stapling of the intestinal sections to one another, while the cylindrical knife 76 cuts a portion of tissue disposed radially inward of the cylindrical knife 76 to complete the anastomosis. At this time, the annular body 110 of the surgical buttress material 100 is attached to the stapled tissue and the tabs 150 of the surgical buttress member 100 are released from the staple cartridge assembly 70.

Persons skilled in the art will understand that the structures and methods specifically described herein and shown in the accompanying figures are non-limiting exemplary embodiments, and that the description, disclosure, and figures should be construed merely as exemplary of particular embodiments. It is to be understood, therefore, that the present disclosure is not limited to the precise embodiments described, and that various other changes and modifications may be effected by one skilled in the art without departing from the scope or spirit of the disclosure.

Additionally, the elements and features shown or described in connection with certain embodiments may be combined with the elements and features of certain other embodiments without departing from the scope of the present disclosure, and that such modifications and variations are also included within the scope of the present disclosure. Accordingly, the subject matter of the present disclosure is not limited by what has been particularly shown and described.

What is claimed is:

1. An apparatus for joining two hollow organ sections with an annular array of surgical staples comprising:

a staple cartridge assembly configured to support the annular array of surgical staples therein, the staple cartridge assembly including pushers configured to eject the respective surgical staples from the staple cartridge assembly, and an outer wall defining a cavity and having a finger deflectably extending over the cavity;

an anvil assembly movable relative to the staple cartridge assembly between spaced apart and approximated positions to adjustably clamp the two hollow organ sections between the staple cartridge and anvil assemblies; and a buttress material including an annular body dimensioned to be mounted on a distal surface of the staple cartridge assembly, and a tab extending proximally from the annular body such that at least a portion of the tab is wrapped around the finger of the outer wall of the staple cartridge assembly, wherein the pushers are movable between a first position in which one of the pushers engages the finger such that the tab of the buttress material wrapped around the finger is secured against the pusher, and a second position in which the one of the pushers is disengaged from the finger such that the at least a portion of the tab of the buttress material wrapped around the finger is released from the one of the pushers.

2. The apparatus according to claim 1, wherein the finger is radially deflectable.

3. The apparatus according to claim 1, wherein the finger is biased radially inward.

4. The apparatus according to claim 1, wherein the annular body of the buttress material includes a planar surface configured to be in planar contact with the distal surface of the staple cartridge assembly.

5. The apparatus according to claim 1, wherein the buttress material includes first and second tabs diametrically opposing each other.

6. The apparatus according to claim 1, wherein the finger of the outer wall of the staple cartridge assembly includes a tooth configured to support the at least a portion of the tab against the one of the pushers.

7. The apparatus according to claim 1, wherein the one of the pushers includes an engaging portion configured to engage the finger of the outer wall of the staple cartridge assembly, the engaging portion being axially tapered.

8. The apparatus according to claim 1, wherein the annular array of surgical staples are ejected from the staple cartridge assembly when the one of the pushers is in the second position.

9. The apparatus according to claim 1, wherein the annular body of the buttress material is concentrically disposed in a juxtaposed relation with the annular array of surgical staples.

10. The apparatus according to claim 1, wherein the staple cartridge assembly further includes a cylindrical knife disposed radially inward of the buttress material.

11. An apparatus for joining two hollow organ sections with an annular array of surgical staples, the apparatus comprising:

a staple cartridge assembly including the annular array of surgical staples and pushers configured to eject the annular array of surgical staples from the staple cartridge assembly;

an anvil assembly movable relative to the staple cartridge assembly between spaced apart and approximated positions to adjustably clamp the two hollow organ sections between the staple cartridge and anvil assemblies; and a buttress material including a body and a tab extending from the body, the body disposed on the staple cartridge assembly such that the body and the annular array of surgical staples are in superposed relation, wherein at least one pusher is transitionable between a first position in which the at least one pusher engages the tab to secure the buttress material to the staple cartridge assembly and a second position in which the at least one pusher is disengaged from the tab to release the buttress material from the staple cartridge assembly.

12. The apparatus according to claim 11, wherein the body of the buttress material has an annular profile configured to be in registration with a distal surface of the staple cartridge assembly.

13. The apparatus according to claim 11, wherein the at least one pusher includes an engaging portion configured to engage the tab of the buttress material, the engaging portion being axially tapered.

14. The apparatus according to claim 11, wherein the annular array of surgical staples are ejected from the staple cartridge assembly when the at least one pusher is in the second position.

15. The apparatus according to claim 11, wherein the staple cartridge assembly includes an outer wall defining a cavity configured to receive the tab therein.

* * * * *